(12) United States Patent
Breslich (10) Patent No.: US 12,285,278 B2
(45) Date of Patent: Apr. 29, 2025

(54) PROTECTIVE VIAL FOR MEDICAL DEVICE (71) Applicant: Conmed Corporation, Utica, NY (US)

(72) Inventor: Grady Breslich, Saint Petersburg, FL (US)

(73) Assignee: Conmed Corporation, Utica, NY (US)

( * ) Notice: Subject to any disclaimer, the term of this patent is extended or adjusted under 35 U.S.C. 154(b) by 361 days.

(21) Appl. No.: 16/711,643

(22) Filed: Dec. 12, 2019

(65) Prior Publication Data

US 2020/0188052 A1 Jun. 18, 2020

Related U.S. Application Data

(60) Provisional application No. 62/779,088, filed on Dec. 13, 2018.

(51) Int. Cl.
*A61B 50/30* (2016.01)
*A61B 17/04* (2006.01)

(52) U.S. Cl.
CPC ...... *A61B 50/3001* (2016.02); *A61B 17/0401* (2013.01); *A61B 2017/0409* (2013.01); *A61B 2017/0416* (2013.01)

(58) Field of Classification Search
CPC ............................................ A61B 2017/0416
See application file for complete search history.

(56) References Cited

U.S. PATENT DOCUMENTS

| | | | | |
|---|---|---|---|---|
| 4,619,644 A | * | 10/1986 | Scott ................. | A61M 25/0668 604/506 |
| 5,423,860 A | * | 6/1995 | Lizardi .............. | A61B 17/0401 606/232 |
| 5,919,160 A | * | 7/1999 | Sanfilippo, II .... | A61M 39/0208 604/93.01 |
| 5,951,518 A | * | 9/1999 | Licata ............... | A61M 25/0097 604/161 |
| 6,080,141 A | * | 6/2000 | Castro ............... | A61M 25/0668 604/164.01 |
| 6,110,146 A | * | 8/2000 | Berthiaume .... | A61M 25/09041 604/103.05 |
| 6,582,390 B1 | * | 6/2003 | Sanderson ........ | A61M 25/0668 600/585 |
| 6,645,178 B1 | * | 11/2003 | Junker .............. | A61M 25/0668 604/164.05 |

(Continued)

*Primary Examiner* — Shaun L David
(74) *Attorney, Agent, or Firm* — Bond, Schoeneck & King, PLLC; Frederick J. M. Price (57) ABSTRACT

A protective device for maintaining the sterilization of a self-drilling anchor inserter and prohibiting the sharp, drilling point of the inserter from puncturing sterile packaging. The device includes a cannulated tube having a proximal end and a distal end. The cannulated tube extends along a longitudinal axis and has proximal and distal portions. The proximal portion extends to the proximal end and the distal portion extends to the distal end. The cannulated tube also has an inner volume. A first slot extends into the inner volume and along the proximal portion toward the proximal end. A second slot extends partially into the cannulated tube between the proximal portion and the distal portion. A connecting portion attaches the proximal portion to the distal portion. The proximal portion is movable relative to the distal portion, between an aligned position and a bent position.

4 Claims, 8 Drawing Sheets

(56) References Cited

U.S. PATENT DOCUMENTS

| | | | | |
|---|---|---|---|---|
| 6,837,873 B1* | 1/2005 | Polley | ............... | A61M 25/0668 |
| | | | | 604/177 |
| 7,303,552 B1* | 12/2007 | Chu | ................... | A61M 25/0668 |
| | | | | 604/263 |
| 2002/0072712 A1* | 6/2002 | Nool | ................. | A61M 25/0136 |
| | | | | 604/164.08 |
| 2003/0032941 A1* | 2/2003 | Boyle | ............... | A61M 25/0668 |
| | | | | 604/533 |
| 2003/0187459 A1* | 10/2003 | Solar | ................ | A61M 25/0668 |
| | | | | 606/129 |
| 2003/0212373 A1* | 11/2003 | Hall | .................. | A61M 25/0668 |
| | | | | 604/263 |
| 2005/0256508 A1* | 11/2005 | Hall | .................. | A61M 25/0668 |
| | | | | 604/529 |
| 2010/0100044 A1* | 4/2010 | Ye | ..................... | A61M 25/0668 |
| | | | | 604/167.03 |
| 2011/0066170 A1* | 3/2011 | Farnan | .................... | A61F 2/962 |
| | | | | 623/1.23 |
| 2012/0061262 A1* | 3/2012 | Merboth | ............... | A61B 50/30 |
| | | | | 53/469 |
| 2013/0018309 A1* | 1/2013 | Ewing | ................ | A61M 25/002 |
| | | | | 604/103.05 |
| 2014/0236147 A1* | 8/2014 | Schneider | ............. | A61B 17/29 |
| | | | | 606/41 |
| 2019/0224459 A1* | 7/2019 | Pedroni | ................ | A61M 25/10 |

* cited by examiner

PROTECTIVE VIAL FOR MEDICAL DEVICE

CROSS-REFERENCE TO RELATED APPLICATION

The present application claims priority to and the benefit of U.S. Provisional Patent Application No. 62/779,088, filed on Dec. 13, 2018 and entitled "Protective Vial for Medical Device," the entirety of which is incorporated herein by reference.

BACKGROUND OF THE INVENTION

1. Field of the Invention

The present invention relates to protective devices for surgical instruments and, more particularly, to a protective vial for an anchor inserter.

2. Description of Related Art

Many orthopedic surgical and medical procedures require the fixation of one body to another body. Such bodies may include bone, soft tissue, and prosthetics. One body can be fixed in a position relative to another using connector devices, such as screws and suture anchors (e.g., cannulated knotless suture anchors and soft all suture anchors). For example, various orthopedic surgeries require the insertion and fixation of a suture anchor within a bone.

One example of a suture anchor is a soft suture anchor, such as the Y-Knot® device. See, e.g., U.S. Pat. No. 9,826,971. Since soft anchors are commonly made entirely of suture materials, they are sometimes called "all-suture" anchors, and generally include a fibrous construct anchor body portion (or fibrous, braided or woven fabric-type structure such as a flexible web, as described in U.S. Pat. No. 9,173,652) and a suture or filament portion. In a traditional Y-Knot device, the suture is pierced entirely through the braid material a number of times, such that the suture passes through a "front" surface and a "back" surface. When a Y-Knot anchor is constructed in the traditional manner, the segments of suture on the back surface of the braid are in contact with bone and can be abraded by the bone due to friction.

There are at least two general, conventional methods for inserting a suture anchor within a bone. In one method, a bone hole is created and prepared using a drill bit. The drill bit is typically advanced through a drill guide to create the bone hole and then, a suture anchor is passed through or down the drill guide into the bone hole for deployment. If the drill guide is moved between creation of the bone hole and advancement of the suture anchor, the drill guide may be moved out of alignment with the bone hole. If the drill guide is no longer aligned with the bone hole, the suture anchor often cannot be inserted and deployed. Therefore, the creation of a second bone hole is often required when drill guide moves out of alignment with the first bone hole.

In a second method, the drilling step is eliminated in an attempt to avoid the aforementioned misalignment issue. A self-punching suture anchor, such as the Y-Knot® RC Suture Anchor, for example, is designed with an inserter that allows the anchor in the inserter to be directly positioned on the bone at the desired location. When the anchor in the inserter is positioned at the desired location, the inserter can be hammered, forcing the anchor directly into the bone. However, hammering the anchor into the bone imparts impact forces to the bone which may be undesirable for some surgical site locations. For example, impact forces may be particularly undesirable at the glenoid bone or smaller bones, such as in the extremities. Further, self-punching anchors are generally required to be larger in size. Thus, such anchors may not only be undesirable but unusable in smaller bones.

To solve the problems with conventional methods for inserting a suture anchor into a bone, a self-drilling anchor inserter was developed. The self-drilling anchor inserter can insert a small suture anchor into the bone without the need to drill a bone hole or to impart impact forces on the bone. However, the self-drilling anchor inserter has a sharp, distal end that can puncture packaging during transportation prior to the surgical procedure.

Therefore, there is a need for a protective device to maintain the sterilization of the inserter and prohibit the sharp, distal end from puncturing sterile packaging.

Description of the Related Art Section Disclaimer: To the extent that specific patents/publications/products are discussed above in this Description of the Related Art Section or elsewhere in this disclosure, these discussions should not be taken as an admission that the discussed patents/publications/products are prior art for patent law purposes. For example, some or all of the discussed patents/publications/products may not be sufficiently early in time, may not reflect subject matter developed early enough in time and/or may not be sufficiently enabling so as to amount to prior art for patent law purposes. To the extent that specific patents/publications/products are discussed above in this Description of the Related Art Section and/or throughout the application, the descriptions/disclosures of which are all hereby incorporated by reference into this document in their respective entirety(ies).

BRIEF SUMMARY OF THE INVENTION

The present disclosure is directed to a protective device for maintaining the sterilization of a self-drilling anchor inserter and prohibiting the sharp, drilling point of the inserter from puncturing sterile packaging. According to an aspect, the protective device includes a cannulated tube having a proximal end and a distal end. The cannulated tube extends along a longitudinal axis and has proximal and distal portions. The proximal portion extends to the proximal end and the distal portion extends to the distal end. The cannulated tube also has an inner volume. One or more slots extend into the inner volume between the proximal end and the distal end of the cannulated tube. The proximal portion of the cannulated tube is movable relative to the distal portion.

According to another aspect, the protective device includes a cannulated tube having a proximal end and a distal end. The cannulated tube extends along a longitudinal axis and has proximal and distal portions. The proximal portion extends to the proximal end and the distal portion extends to the distal end. The cannulated tube also has an inner volume. A first slot extends into the inner volume and along the proximal portion toward the proximal end. A second slot extends partially into the cannulated tube between the proximal portion and the distal portion. A connecting portion attaches the proximal portion to the distal portion.

According to yet another aspect, the present invention is a protected anchor inserter assembly. The assembly includes (i) a protective device having: a cannulated tube having a proximal end and a distal end and extending along a longitudinal axis, a proximal portion of the cannulated tube extending to the proximal end, a distal portion of the cannulated tube extending to the distal end, an inner volume extending through the cannulated tube, one or more slots extending into the inner volume between the proximal end and the distal end of the cannulated tube, wherein the proximal portion is movable relative to the distal portion; and (ii) an anchor inserter having a shaft with a proximal end and a sharp distal end. The anchor inserter extends along the longitudinal axis within the inner volume of the cannulated tube.

BRIEF DESCRIPTION OF THE SEVERAL VIEWS OF THE DRAWING(S)

The present invention will be more fully understood and appreciated by reading the following Detailed Description in conjunction with the accompanying drawings. The accompanying drawings illustrate only typical embodiments of the disclosed subject matter and are therefore not to be considered limiting of its scope, for the disclosed subject matter may admit to other equally effective embodiments. Reference is now made briefly to the accompanying drawings, in which.

DETAILED DESCRIPTION OF THE INVENTION

Figure 1:
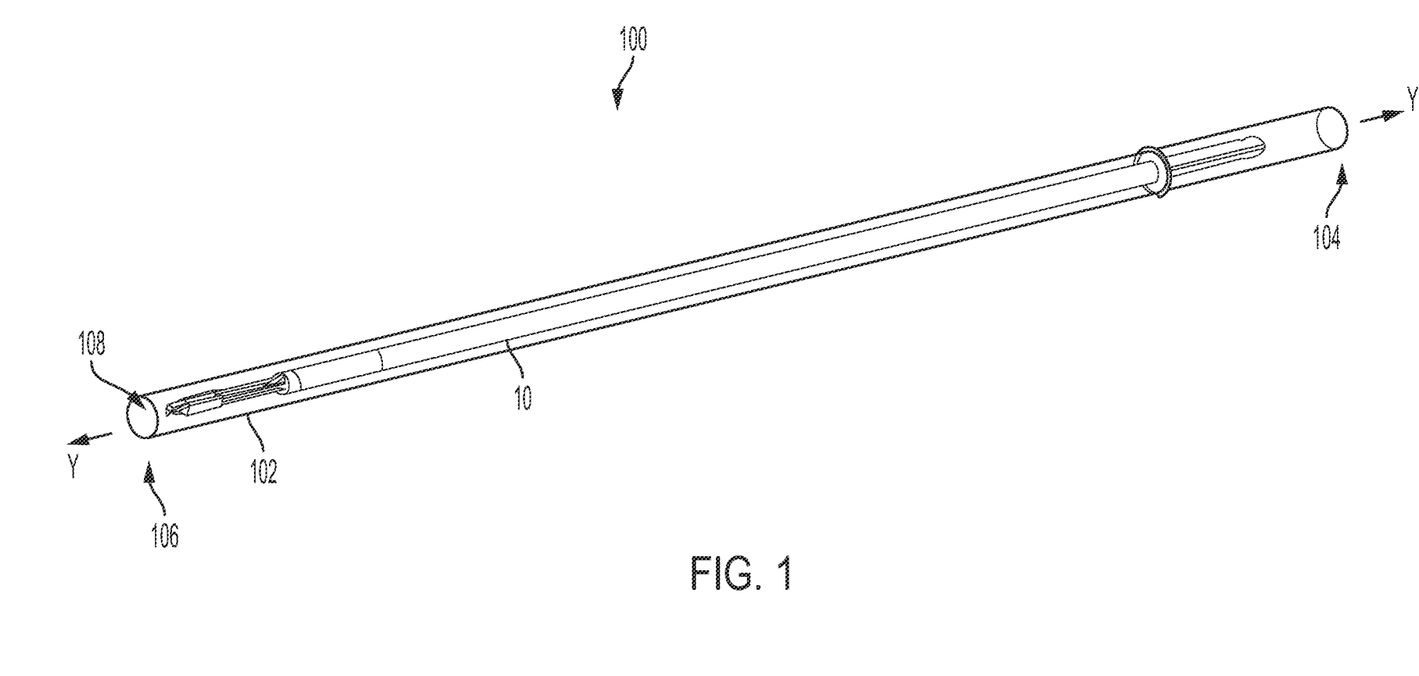
FIG. 1 is a perspective view schematic representation of a protective device, according to an embodiment.

Referring now to the drawings, wherein like reference numerals refer to like parts throughout, there is seen in FIG. 1, a perspective view schematic representation of a protective device 100, according to an embodiment. The protective device 100 comprises a cannulated tube 102 having a proximal end 104 and a distal end 106. The cannulated tube 102 extends along a central longitudinal y–y axis. The cannulated tube 102 has an inner volume 108 sized and configured to fit a self-drilling anchor inserter 10 therein.

Figure 2A:
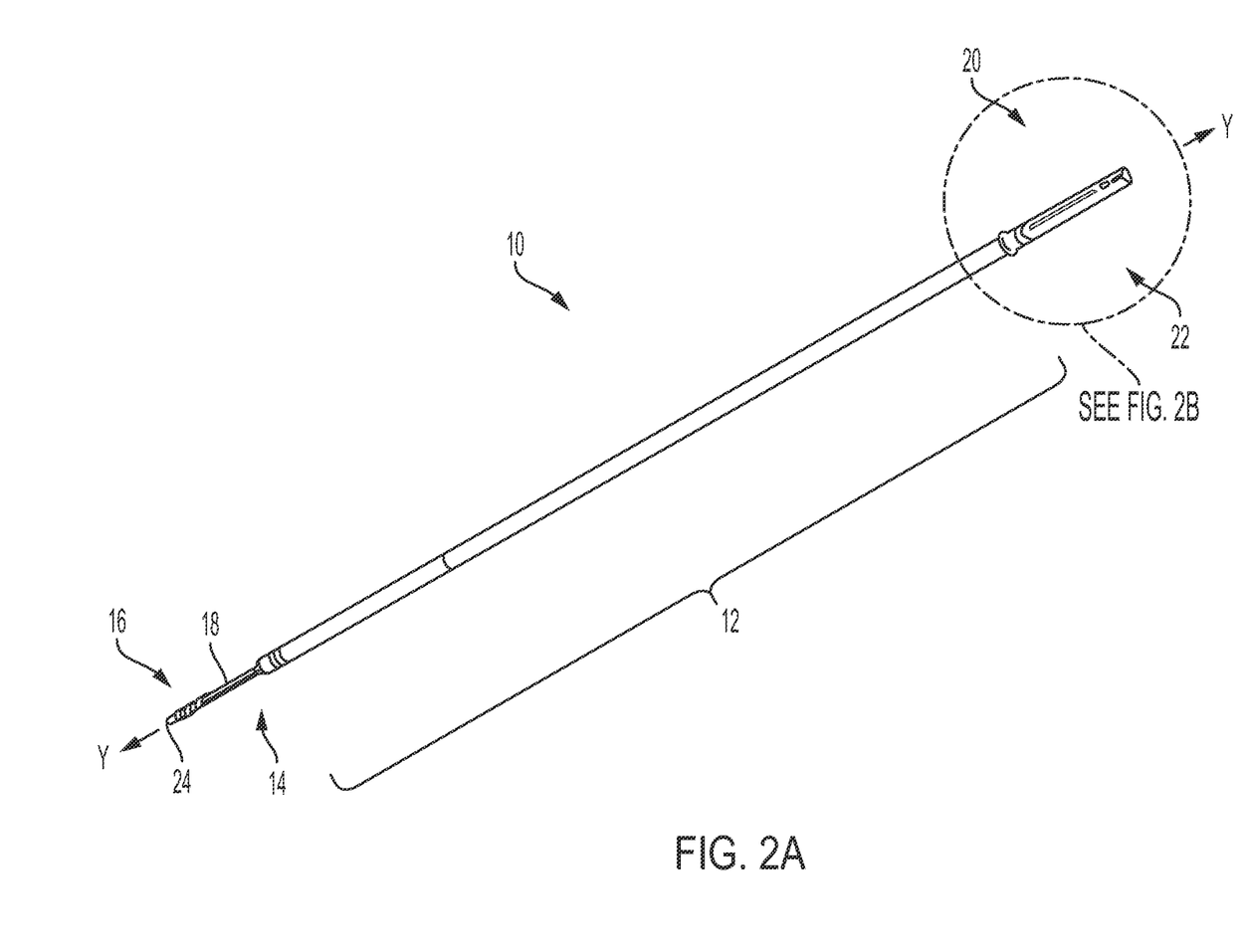
FIG. 2A is a perspective view schematic representation of a self-drilling anchor inserter, according to an exemplary embodiment.

An exemplary embodiment of the self-drilling anchor inserter 10 is shown and described in PCT/US2018/043446, entitled "Self-Drilling All-Suture Anchor Inserter" and incorporated herein in its entirety by reference. FIG. 2A shows a perspective view schematic representation of an exemplary embodiment of the self-drilling anchor inserter 10. The inserter 10 is generally composed of metal, such as stainless steel or nitinol; however, other suitable materials with sufficient strength to handle the forces required to drill and insert an anchor may be used (as should be understood by a person of ordinary skill in the art in conjunction with a review of this disclosure). Further, different features of the inserter 10 may be composed of different materials. For example, a sufficiently small diameter nitinol can be used for a length 12 of the inserter 10 to allow the inserter 10 to have the required flexibility to pass and operate in a curved guide tube to reach a desired insertion location. In another example, a sufficiently large diameter stainless steel can be used for the length 12 of the inserter 10 to allow the inserter 10 to have the required stiffness to be located at the desired insertion location and operate under its own support without the use of a guide tube.

As shown in FIG. 2A, the inserter 10 comprises a distal end 14 having an inserter tip 16 connected to a shaft 18, which extends proximally along the central longitudinal y–y axis to connect to a power handpiece interface, such as a quick change connector 22, at the proximal end 20 of the inserter 10. A quick change connector 22 refers generally to a feature that facilitates the use of a power attachment for drilling.

The inserter tip 16 comprises a sharp, drilling point 24. In an embodiment, the inserter tip 16 comprises a suture anchor retention slot (not shown) sized or otherwise configured to hold an anchor braid and length of suture of an all-suture anchor, permitting the all-suture anchor to be pushed into a bone hole created by the sharp, drilling point 24.

Figure 2B:
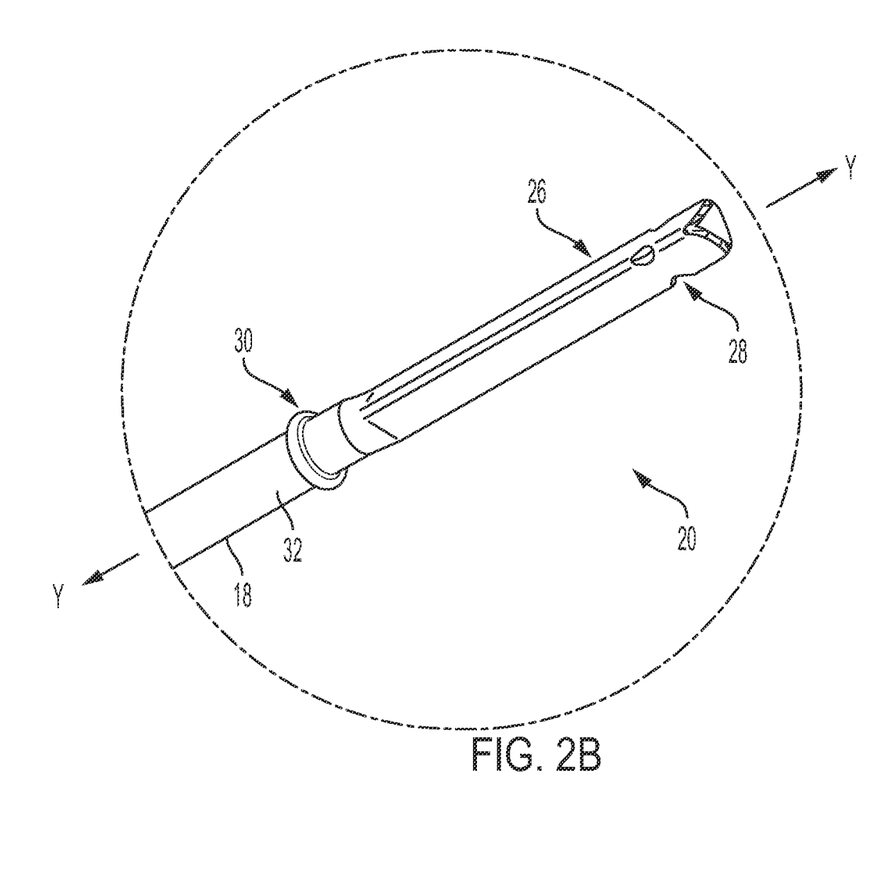
FIG. 2B is a detail view of the proximal end of the self-drilling anchor inserter of FIG. 2A.

Referring now to FIG. 2B, there is shown a detail view of the proximal end 20 of the self-drilling anchor inserter 10 of FIG. 2A. In the depicted embodiment, the quick change connector 22 attached to the shaft 18 comprises three flat surfaces 26, having a triangular cross-section. The shaft 18 also comprises three grooves 28, which extend into the shaft 18 at positions wherein the two of the three flat surfaces 26 meet or otherwise converge, as shown in FIG. 2B. In an embodiment, the quick change connector 22 is compatible with a traditional AO connection and other connections, such as a Trinkle or Hudson connection can be used (as should be understood by a person of ordinary skill in the art in conjunction with a review of this disclosure). In the depicted embodiment, the three flat surfaces 26 permit the central longitudinal y–y axis of the inserter 10 to be co-linear with a central longitudinal y–y axis extending through a grasping chuck (not shown).

The quick change connector 22 can be formed from a solid piece of metal or formed into the end of tubing. Forming the quick change connector 22 into tubing offers many advantages for use with the inserter 10. For example, the proximal end 20 is kept open to allow better flow of ethylene oxide (EO) for sterilization of the suture material housed inside the tubing and there can be a reduction in the number of components needed for assembly of the inserter 10.

The inserter 10 also includes a proximal hard stop feature 30 on the inserter 10, as shown in FIG. 2B. In the depicted embodiment, a hard stop feature 30 is positioned or otherwise located along the proximal end 20 of the inserter 10. The hard stop feature 30 is distal relative to the quick change connector 22 such that the hard stop feature 30 prevents the quick change connector 22 from entering or advancing through a guide. In the depicted embodiment, the hard stop feature 30 is a ring wrapped around an outer surface 32 of the inserter 10. However, any other shape or configuration for a hard stop feature 30 can be used if sufficiently sized larger than a diameter of the guide.

Figure 3:
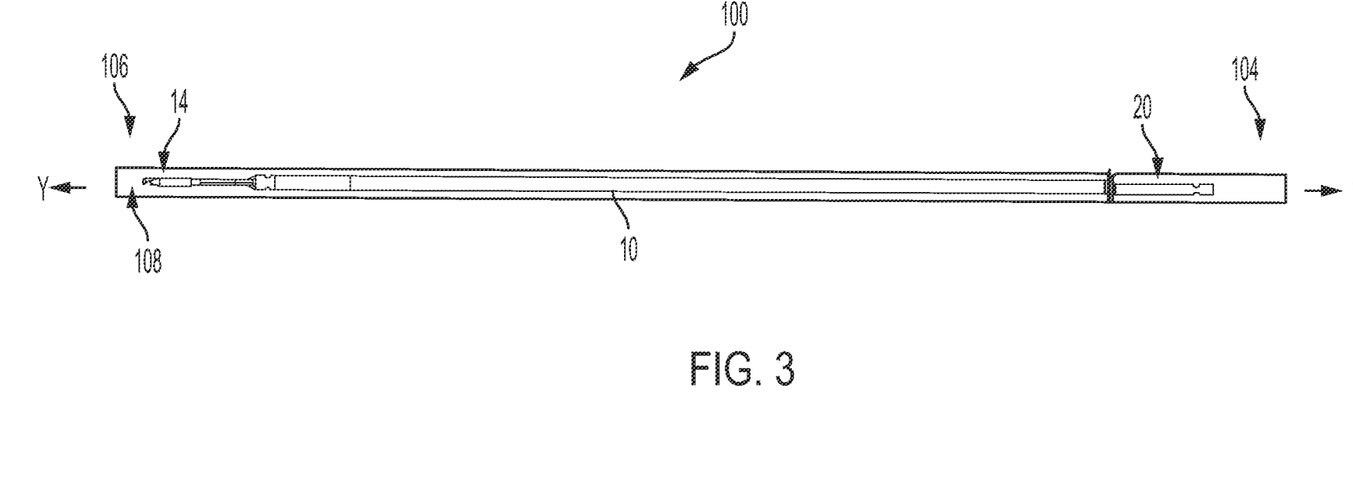
FIG. 3 is a side view schematic representation of the protective device, according to an embodiment.

Referring now to FIG. 3, there is shown a side view schematic representation of the protective device 100, according to an embodiment. As shown in FIG. 3, the self-drilling anchor inserter 10 is positioned within the inner volume 108 of the protective device 100 such that the distal end 14 of the inserter 10 is at the distal end 106 of the protective device 100 and the proximal end 20 of the inserter 10 is at the proximal end 104 of the protective device 100. The positioning of the inserter 10 within the inner volume 108 of the protective device 100 can be important due to accessibility features at the proximal end 104 of the protective device 100 described below.

Figure 4:
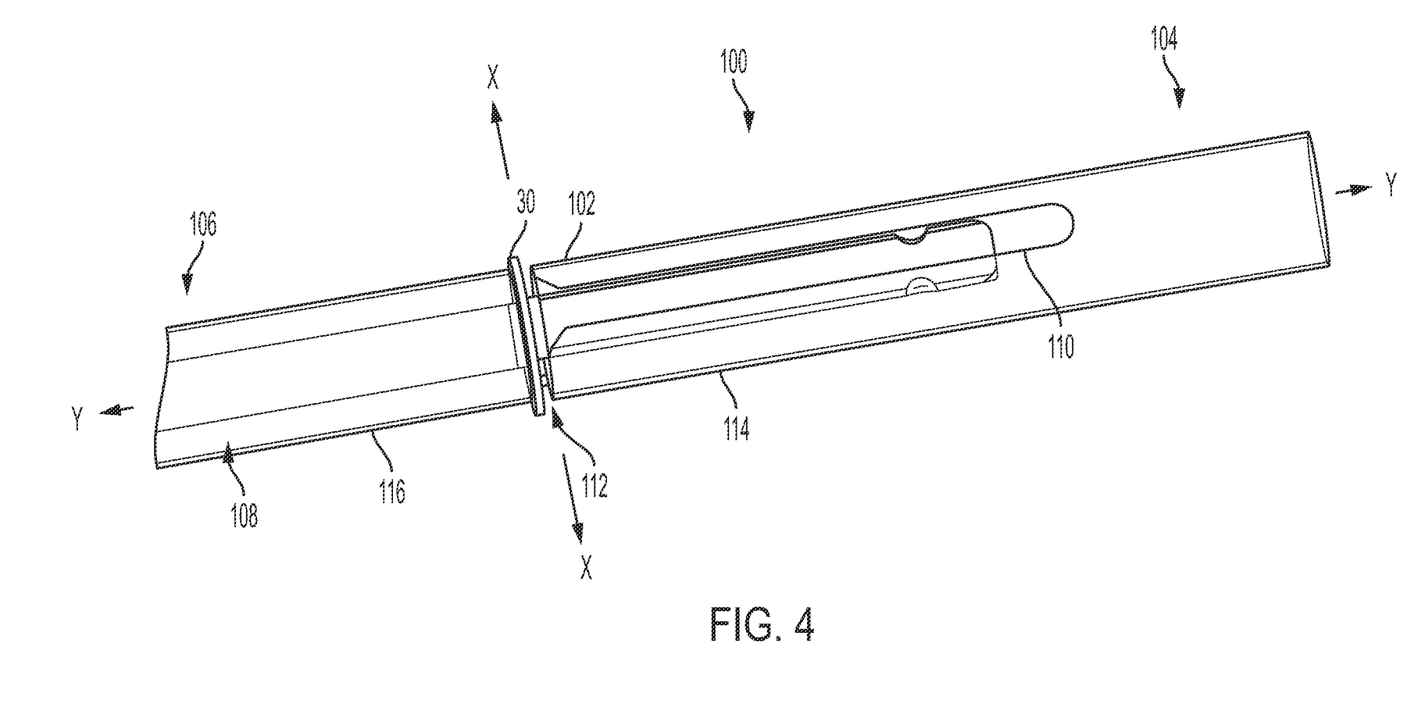
FIG. 4 is a close-up perspective view schematic representation of the proximal end of the protective device, according to an embodiment.

Turning now to FIG. 4 there is shown a close-up perspective view schematic representation of the proximal end 104 of the protective device 100, according to an embodiment. As shown, the proximal end 104 of the protective device 100 comprises a first slot 110 extending through the cannulated tube 102. The first slot 110 can be any type of cutout extending through the cannulated tube 102 and into the inner volume 108. The first slot 110 extends through the cannulated tube 102 along the central longitudinal y–y axis toward, but not up to, the proximal end 104 of the protective device 100.

Still referring to FIG. 4, the cannulated tube 102 also comprises a second slot 112. The second slot 112 traverses the cannulated tube 102 and the central longitudinal y–y axis. The second slot 112 can be any type of cutout extending through the cannulated tube 102 and into the inner volume 108. In an embodiment, the second slot 112 extends along an x–x axis, which is substantially perpendicular to the central longitudinal y–y axis. The second slot 112 extends partially, not entirely, through the cannulated tube 102. The second slot 112 creates a proximal portion 114 and a distal portion 116 of the cannulated tube 102. The proximal portion 114 extends from the second slot 112 to the proximal end 104 of the cannulated tube 102 and the distal portion 116 extends from the second slot 112 to the distal end 106 of the cannulated tube 102.

As also shown in FIG. 4, the hard stop feature 30 on the inserter 10 is positioned within the second slot 112. In some embodiments, such as that shown in FIG. 4, the hard stop feature 30 has a diameter greater than a diameter of the cannulated tube 102. Therefore, the hard stop feature 30 extends partially out from the cannulated tube 102 via the second slot 112.

Figure 5:
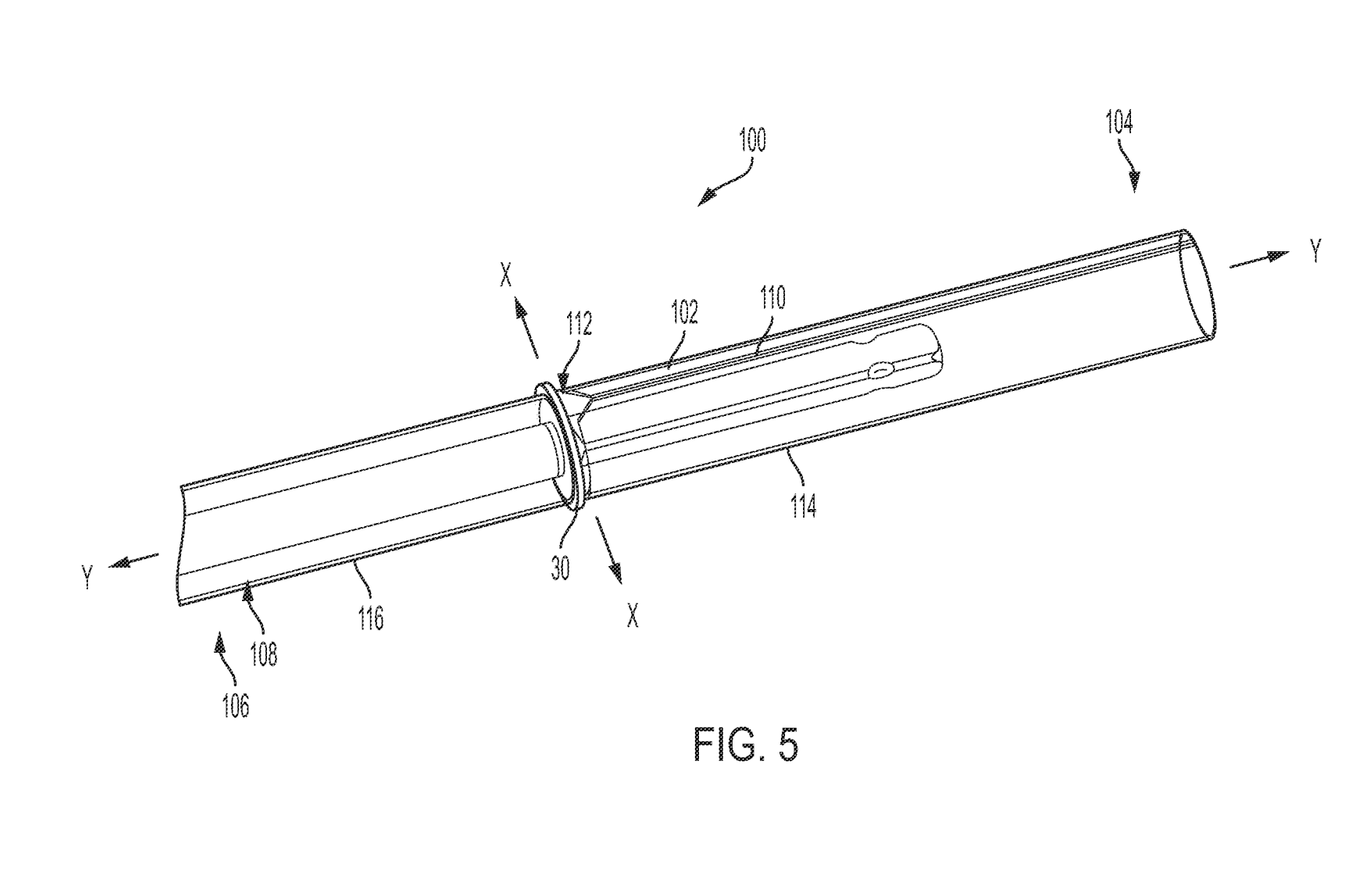
FIG. 5 is a close-up perspective view schematic representation of the proximal end of the protective device in the aligned position, according to an embodiment.

Turning now to FIG. 5, there is shown a close-up perspective view schematic representation of the proximal end 104 of the protective device 100 in an aligned position, according to an embodiment. As stated above, the first slot 110 extends toward and not up to the proximal end 104 and the second slot 112 extends only partially through the cannulated tube 102. The purpose of first and second slots 110, 112 is to facilitate access to the proximal end 104 of the inserter 10. The first and second slots 110, 112 create the movable proximal portion 114 of the cannulated tube 102 and the stationary distal portion 116. In an aligned position shown in FIG. 5, the proximal portion 114 extends along the central longitudinal y–y axis such that the proximal portion 114 is aligned with the distal portion 116 of the cannulated tube 102.

Figure 6:
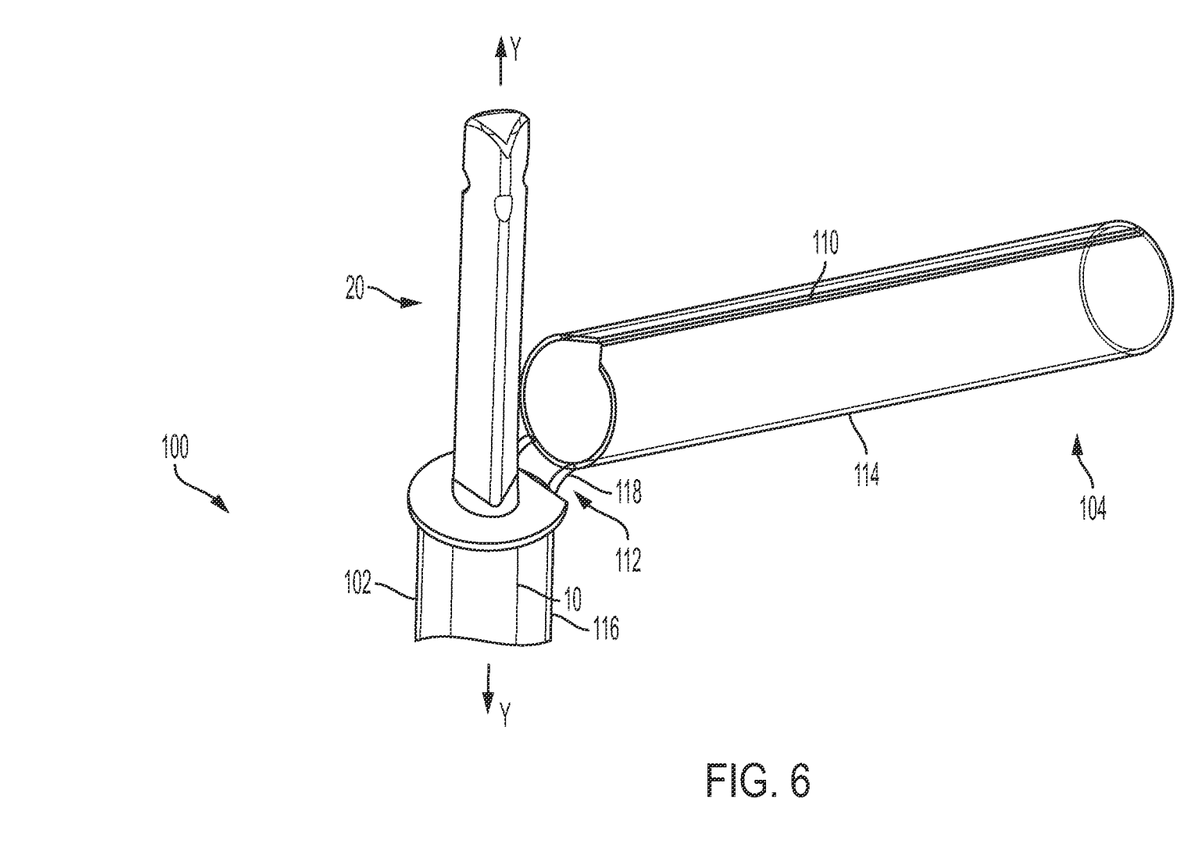
FIG. 6 is a close-up perspective view schematic representation of the proximal end of the protective device in the bent position, according to an embodiment.

To access the proximal end 104 of the inserter 10, the user bends the proximal portion 114 from the aligned position (FIG. 5) to a bent position (FIG. 6). In the bent position, the proximal portion 114 extends at an angle relative to the central longitudinal y–y axis and the distal portion 116 of the cannulated tube 102, as shown in FIG. 6. The geometry and positioning of the first and second slots 110, 112 allows the user to grasp the protective device 100 while bending the proximal portion 114 with his or her thumb.

Still referring to FIG. 6, the proximal portion 114 of the cannulated tube 102 can bend without breaking due to the arrangement of the first and second slots 110, 112 and the composition of the cannulated tube 102. As the proximal portion 114 begins to bend and move from the aligned position to the bent position, the proximal end 20 of the inserter 10 begins to move through the first slot 110. In the depicted embodiment, the first slot 110 has a length that is equal to or larger than the a length of the proximal end 20 of the inserter 10 such that the proximal end 20 of the inserter 10 can easily slide through the first slot 110.

The proximal portion 114 remains attached to the remainder of the cannulated tube 102 in the bent position due to the configuration of the second slot 112. As the second slot 112 extends only partially through the cannulated tube 102, a connecting portion 118 of the cannulated tube 102 connects the distal portion 116 of the cannulated tube 102 to the proximal portion 114 of the cannulated tube 102, as shown in FIG. 6. The connecting portion 118 and the proximal portion 114 of the cannulated tube 102 are bendable because they are composed of a sturdy yet flexible plastic material. Such flexible plastic material may include PETG (Polyethylene Terephthalate, Glycol Modified), HDPE (High density polyethylene), LDPE (Low density polyethylene), polypropylene, and others. As a result, the proximal portion 114 does not need to be discarded or otherwise disposed of after use.

Prior to use in a surgical procedure, the self-drilling anchor inserter 10 is within the protective device 100, as shown in FIGS. 1 and 2. As described above, the drilling point 24 of the self-drilling inserter 10 is sharp. The protective device 100 protects the drilling point 24 of the inserter 10 during shipping and handling prior to use. Typically, the inserter 10 is shipped within a sealed pouch 120 such as that shown in FIG. 7. The pouch 120 is generally composed of nylon (e.g., Tyvek), which although suitable for ethylene oxide (EO) sterilization, is susceptible to puncture by the sharp, drilling point 24 of the inserter 10. With the sharp, distal end 106 of the inserter 10 enclosed or otherwise surrounded by the distal end 106 of the protective device 100, the inserter 10 can be safely transported.

Figure 7:
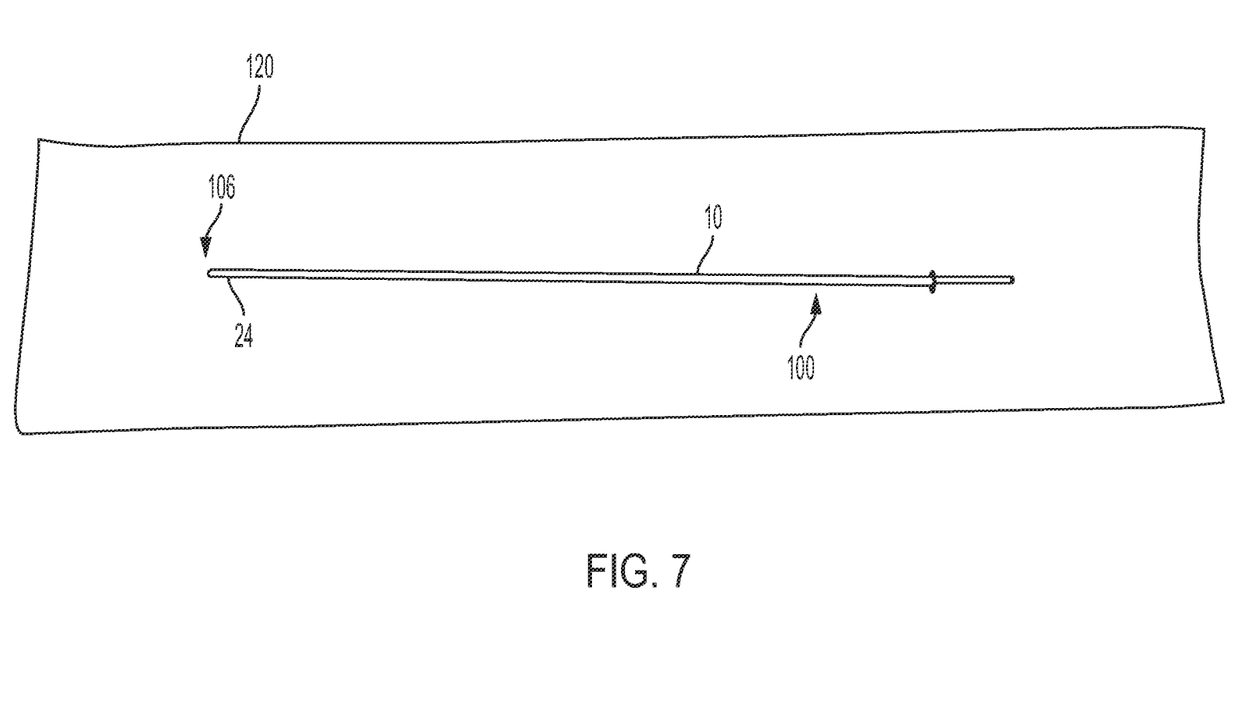
FIG. 7 is a perspective view schematic representation of the protective device in a pouch, according to an embodiment.

For surgical use, a non-sterile user can open the pouch 120 using the typical sterile technique. This allows a sterile user to remove the protective device 100 from the pouch 120. With the proximal end 104 of the protective device 100 presented, the sterile user can grasp the protective device 100 near or distal to the proximal portion 114 and move the proximal portion 114 to the bent position. With the proximal portion 114 in the bent position, the user can then attach the proximal end 104 of the inserter 10 directly to a compatible drill hand piece and completely remove the inserter 10 from the protective device 100 for use.

While embodiments of the present invention has been particularly shown and described with reference to certain exemplary embodiments, it will be understood by one skilled in the art that various changes in detail may be effected therein without departing from the spirit and scope of the invention as defined by claims that can be supported by the written description and drawings. Further, where exemplary embodiments are described with reference to a certain number of elements it will be understood that the exemplary embodiments can be practiced utilizing either less than or more than the certain number of elements.

What is claimed is:

1. A protected anchor inserter assembly, comprising:
 a protective device having:

a cannulated tube having a proximal end and a distal end and extending along a longitudinal axis;
a proximal portion of the cannulated tube extending to the proximal end;
a distal portion of the cannulated tube extending to the distal end;
an inner volume extending through the cannulated tube;
one or more slots extending into the inner volume between the proximal end and the distal end of the cannulated tube; and
wherein the proximal portion is movable relative to the distal portion;
an anchor inserter having a shaft with a proximal end and a sharp distal end, a hard stop feature around an outer surface of the shaft of the anchor inserter, wherein the hard stop feature extends through one of the one or more slots in the protective device; and
wherein the anchor inserter extends along the longitudinal axis within the inner volume of the cannulated tube.

2. The assembly of claim 1, wherein the proximal end of the anchor inserter extends toward the proximal end of the cannulated tube and the sharp distal end of the anchor inserter extends toward the distal end of the cannulated tube.

3. The assembly of claim 1, further comprising a quick change connector at the proximal end of the shaft wherein the quick change connector is positioned within the proximal portion of the cannulated tube.

4. The assembly of claim 1, wherein the proximal portion is movable to a bent position wherein the proximal end of the shaft is outside the cannulated tube.

* * * * *